(12) United States Patent
Jochim et al.

(10) Patent No.: US 7,632,527 B2
(45) Date of Patent: Dec. 15, 2009

(54) COMPOSITIONS FOR JUICE-BASED PEELS AND MASKS

(75) Inventors: Melissa Jochim, Novato, CA (US); Karen Behnke, San Anselmo, CA (US)

(73) Assignee: Juice Beauty, San Rafael, CA (US)

( * ) Notice: Subject to any disclaimer, the term of this patent is extended or adjusted under 35 U.S.C. 154(b) by 0 days.

(21) Appl. No.: 11/933,409

(22) Filed: Oct. 31, 2007

(65) Prior Publication Data

US 2008/0166312 A1    Jul. 10, 2008

Related U.S. Application Data

(63) Continuation-in-part of application No. 11/264,549, filed on Nov. 1, 2005.

(51) Int. Cl.
- *A61K 36/00* (2006.01)
- *A61K 36/28* (2006.01)
- *A61K 36/752* (2006.01)
- *A61K 36/87* (2006.01)
- *A61K 36/886* (2006.01)
- *A61K 36/20* (2006.01)
- *A61K 36/82* (2006.01)
- *A61K 31/00* (2006.01)

(52) U.S. Cl. .................. 424/725; 424/765; 424/736; 424/766; 424/744; 424/535; 424/729; 514/1

(58) Field of Classification Search .................. None
See application file for complete search history.

(56) References Cited

U.S. PATENT DOCUMENTS

| | | |
|---|---|---|
| 4,699,930 A | 10/1987 | Suga |
| 5,523,090 A | 6/1996 | Znaiden et al. |
| 6,280,751 B1 | 8/2001 | Fletcher et al. |
| 6,471,972 B1 | 10/2002 | Bonte et al. |
| 6,482,442 B1 | 11/2002 | Dado |
| 2003/0069618 A1 | 2/2003 | Smith et al. |
| 2003/0147830 A1 | 8/2003 | Phillips et al. |
| 2004/0180033 A1 | 9/2004 | Msika |
| 2005/0031573 A1 | 2/2005 | Cho et al. |
| 2005/0063932 A1 | 3/2005 | Dilallo et al. |
| 2005/0214244 A1 | 9/2005 | Fleming |
| 2006/0204467 A1 | 9/2006 | Litter et al. |
| 2007/0071780 A1 | 3/2007 | Dubois et al. |
| 2007/0098670 A1 | 5/2007 | Jochim et al. |

OTHER PUBLICATIONS

"Juice Beauty: Green Apple Peel". Internet Archive Date: Oct. 27, 2005 [Retrieved from the Internet: Sep. 20, 2008]. Retrieved from: <http://web.archive.org/web/20051027183054/www.juicebeauty.com/Merchant2/merchant.mv?Screen=PROD&Store_Code=J&Product_Code=277301>.*

"Juice Beauty: Green Apple Nutrient Mask". Internet Archive Date: Oct. 27, 2005 [Retrieved from the Internet: Sep. 20, 2008]. Retrieved from: <http://web.archive.org/web/20051027182647/www.juicebeauty.com/Merchant2/merchant.mv?Screen=PROD&Store_Code=J&Product_Code=277305>.*

International Search Report for PCT/US06/60345 filed Oct. 30, 2006—mailing date of Nov. 1, 2007.

* cited by examiner

*Primary Examiner*—Christopher R Tate
*Assistant Examiner*—Amy L Clark
(74) *Attorney, Agent, or Firm*—Townsend and Townsend and Crew LLP

(57) ABSTRACT

The disclosure herein is directed to organic skin-based products that comprise an excess of 70% organic ingredients. The skin care products described herein are composed of a plurality of organic juices and other organic materials.

9 Claims, 3 Drawing Sheets

COMPOSITIONS FOR JUICE-BASED PEELS AND MASKS

RELATED APPLICATIONS INFORMATION

This application claims priority as a Continuation-In-Part under 35 U.S.C. § 120 to U.S. patent application Ser. No. 11/264,549, filed Nov. 1, 2005 and entitled "Compositions and Methods for Using Juice Organic, Juice Based Skin Care Products." The disclosures of the above-identified applications are incorporated herein by reference as if set forth in full.

BACKGROUND

1. Field of the Invention

This disclosure relates to skin care products, and more particularly to juice based skin care compositions and methods for using juice based skin care products.

2. Background of the Invention

There are hundreds of skin care products on the market today designed to provide a variety of benefits and care for hands, feet, body, eyes, face, etc. The effectiveness of these skin care products varies widely, however, and in addition to being ineffective, many of them can have adverse side effects and can even damage the skin. This is especially true for sensitive and/or blemish-prone skin.

The main ingredient in all conventional skin care products is water. In fact, over 50% of many conventional skin care products can be made up of water. Further, conventional skin care products can also include artificial fillers, preservatives, tars, petroleum, synthetic fragrances, and parabens. All of these ingredients are absorbed by the skin when the skin care product is applied, and can cause such problems as blemishes, dry skin, rashes, etc.

SUMMARY

The disclosure herein is directed to organic skin-based products that comprise an excess of 70% organic ingredients. For example, the skin care products described herein are composed of a plurality of organic juices and other organic materials.

In one aspect, the organic skin care products described can be used in a variety of skin care solutions to achieve various skin care objectives.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which.

DETAILED DESCRIPTION

Figure 1:
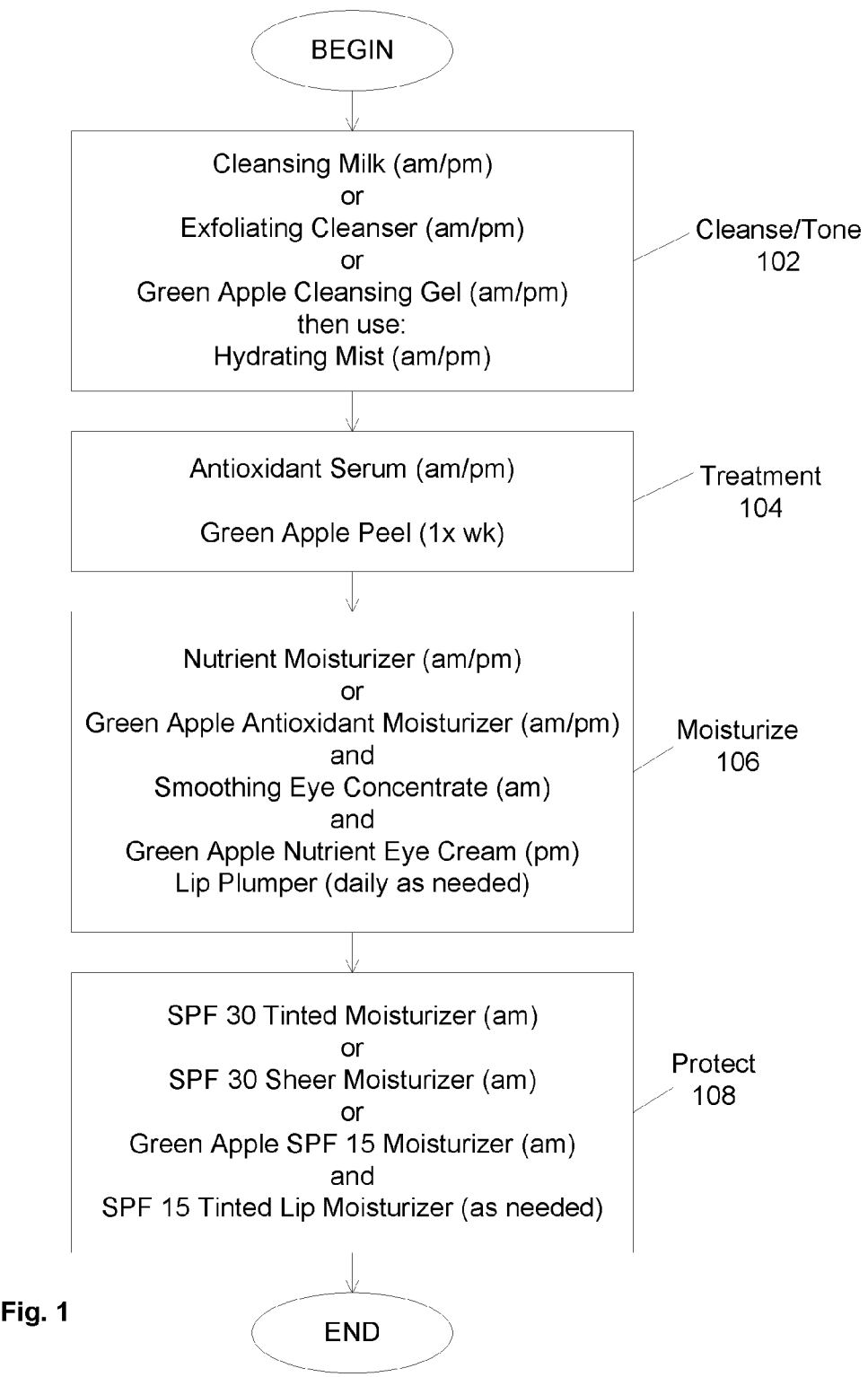
FIG. 1 is a flowchart illustrating one example skin care solution that makes use of organic skin care products in accordance with one embodiment.

The embodiments described below are directed to compositions for organic skin care products. The percentage of organic ingredients in each of the compositions is an excess of 70% in accordance with the USDA National Organic Program food standards. In particular, the main ingredient in each of the compositions are organic fruit juices. The organic fruit juices are used in place of water as used in conventional skin care products. By using organic fruit juices in the place of water, the compositions below can achieve the 70% or greater USDA food standard.

Using organic juices as a base composition for a skin care product is a costly process with many challenging logistics. For example, seasonal produce, weather sensitivity and the fact that each crop has unique chemistry and colors combine to make the development of juice-based organic skin care products extremely difficult; however, the compositions described below have been shown to produce repeatable results.

Each of the compositions below has a unique blend of organic juices with a specific benefit for the skin type being targeted; however, the same juices, such as apple, white grape, red grape, lemon juice, to name just a few, are used in each of the compositions. In fact, up to 25 organic juices can be found in the compositions described herein. Organic juices are rich in potent antioxidants, essential vitamins, vital phytonutrients, and powerful hydroxy acids, making them excellent ingredients for skin care products. The compositions below result in skin care products that are quite concentrated, but beneficial for the skin. It will be clear that the compositions below do not make use of any artificial fillers, toxic preservatives, water to dilute the compositions, tars, petroleum, synthetic fragrances, or parabens.

The following descriptions are related to several example skin care products and compositions. The following examples should not be seen as limiting the products and compositions described herein to any particular products and compositions however. It will be understood, that many more products and compositions are possible. These new products and compositions can comprise minute to substantial variations on the products and compositions described herein, or can comprise entirely new products and compositions. Thus, the products and compositions described below are presented by way of example only.

A first example of an organic, juice-based skin care product is a nutrient moisturizer. In one embodiment, an organic, juice-based nutrient moisturizer can include one or more of the following organic ingredients: an organic juice base, e.g., *VITIS vinifera* (white grape) juice, *DAUCUS carota* sativa (carrot) juice and *ALOE barbadensis* leaf juice. Further, the ingredients can include organic botanical extracts of *CALENDULA officinalis* flower, *MATRICARIA chamomilla* flower, *TILIA europea* (linden) leaf and *ROSE canina* (rosehip) fruit, glycerin, organic plant oils of *BUTYROSPERMUM parkii* (shea butter) and *SIMMONDSIA chinensis* (jojoba) seed, organic essential fatty acids of *OENOTHERA biennis* (evening primrose), *LINUM usitatissimum* (linseed) seed and *BORAGO officinali* (borage) seed, organic honey, *VITIS vinifera* (grape) seed oil, organic algae extract, squalane, *LIMNANTHES alba* (meadow foam) seed oil, tocopheryl acetate (vitamin E), retinyl palmitate (vitamin A), magnesium ascorbyl phosphate (vitamin C), panthenol (vitamin B5), hyaluronic acid, hydroxypropyl starch phosphate, glyceryl stearate, potassium sorbate, phospholipids, beta carotene, palmitic acid, stearic acid, cetearyl glucoside, xanthan gum, disodium edta, sodium hydroxide, benzyl alcohol, and phenoxyethanol.

Moreover, the ingredients described above can include blends of pure essential oils produced by and for Juice Beauty, Inc. located in California, 94901 and at the website www.juicebeauty.com. These pure essential oils can include

*LITSEA cubeba* (may chang), cananga odorata (ylang ylang), *BOSWELLIA carterii* (frankincense) and *COMMIPHORA myrrha* pure essential oils.

Importantly, no parabens are used in the composition of a moisturizer using the ingredients listed above. Further, the ingredients do not contain any harsh cleansers, which can have adverse effects on the skin. The ingredients are combined in the manner to produce a moisturizer that is at least 70% organic and is as high as even 94% organic.

Further, azulene can be added to the ingredients to form a green apple moisturizer. The green apple moisturizer can have a green apple smell and color. Additionally, green apple moisturizer can include an active ingredient such as titanium dioxide, etc. Antioxidants can also be added to the moisturizer to form green apple antioxidant moisturizer.

Another example of an organic, juice-based product can be a Green Apple antioxidant serum. In one embodiments, such a hydroxy-acid antioxidant serum can comprise an organic alpha and betahydroxy acid juice base, e.g., comprising *PYRUS malus* (apple) juice (malic), *CITRUS medica* limonum (lemon) juice (citric), *VITUS vinifera* (white grape) juice (tartaric), organic raw cane sugar (glycolic), willow bark extract (salicylic), organic milk peptides (lactic), organic *ALOE barbadensis* (leaf juice).

Further, the ingredients can include glycerin; organic *CAMELLIA sinensis* (green tea) leaf extract; organic algae extract; *VITUS vinifera* (grape) seed oil; organic essential fatty acids, e.g., *OENOTHERA biennis* (evening primrose), *LINUM usitatissimum* (linseed) seed, and *BORAGO officinali* (borage) seed; ubiquinone (coenzyme Q10); thioctic acid (alpha-lipoic acid); dipeptide-2 and palmitoyl tetrapeptide-3; magnesium ascorbyl phosphate (vitamin C); tocopheryl acetate and tocopherol (vitamin E); retinol palmitate (vitamin A); sclerotium gum; dimethylaminoethanol (DMAE); phenoxyethanol; sodium hydroxide; benzyl alcohol; disodium edta; phospholipids; hyaluronic acid; and potassium sorbate.

Further, the antioxidant serum described above can include Juice Beauty essential oils, such as *CITRUS reticulata* (mandarin), *LITSEA cubeba* (may chang) and *CINNAMOMUM camphora* (ho wood) pure essential oils.

Further, azulene can be added to the ingredients to form a green apple antioxidant serum. The green apple antioxidant serum can have a green apple smell and color.

Another example of an antioxidant serum can comprise an organic juice base of *VITIS vinifera* (white grape) juice, *CITRUS aurantium* dulcis (orange) juice, and *ALOE barbadensis* leaf juice. The serum can further comprise glycerin, *VITIS vinifera* (grape) seed oil, organic essential fatty acids of *OENOTHERA biennis* (evening primrose), *LINUM usitatissimum* (linseed) seed, and *BORAGO officinali* (borage) seed, organic algae extract, ubiquinone (coenzyme Q10), thioctic acid (alpha-lipoic acid), magnesium ascorbyl phosphate (vitamin C), dipeptide-2, palmitoyl tetrapeptide-3, tocopheryl acetate, and tocopherol (vitamin E), retinyl palmitate (vitamin A), sclerotium gum, phenoxyethanol, sodium hydroxide, benzyl alcohol, disodium edta, phospholipids, hyaluronic acid, dimethylaminoethanol (DMAE), and potassium sorbate.

Further, the antioxidant serum described above can include Juice Beauty essential oils, such as *AMYRIS balsamifera* and *LITSEA cubeba* (may chang) pure essential oils.

A green apple mousse body cleanser is another example. Its ingredients can include: organic juices of *PYRUS malus* (apple) juice (malic), *CITRUS medica* limonum (lemon) juice (citric) & *ALOE barbadensis* leaf juice, organic *SACCHARUM officinarum* (glycolic acid), organic botanical extracts of *TARAXACUM officinale* (dandelion) leaf, *MELISSA officinalis* (lemon balm) leaf & *SALVIA officinalis* (sage) leaf, organic algae extract, glycerin, organic honey, sodium carboxymethyl lauryl glucoside, cocamidopropyl betaine, tocopheryl acetate & tocopherol (vitamin E), retinyl palmitate (vitamin A), phenoxyethanol, benzyl alcohol, potassium sorbate, sodium hydroxide, and limonene.

Further, the green apple mousse body cleanser described above can include Juice Beauty essential oils, such as *CITRUS reticulata* (mandarin), *LITSEA cubeba* (may chang) and *CINNAMOMUM camphora* (ho wood) pure essential oils.

A nourishing cleanser is another example. Its ingredients can include: organic juices of *VITIS vinifera* (white grape) juice, *PYRUS malus* (apple) juice & *ALOE barbadensis* leaf juice, organic botanical extracts of *CALENDULA officinalis* flower & *MATRICARIA chamomilla* flower, glycerin, organic plant oils of carthamus tinctorius (safflower) seed & *HELIANTHUS annuus* (sunflower), caprylic/capric triglyceride, cetearyl alcohol, cetearyl glucoside, sorbitan stearate, tocopheryl acetate & tocopherol (vitamin E), ascorbyl palmitate (vitamin C), tetrasodium edta, panthenol (vitamin B5), allantoin, phenoxyethanol, xanthan gum, benzyl alcohol, potassium sorbate, citric acid, limonene, and linalool.

Further, the nourishing cleanser described above can include Juice Beauty essential oils, such as *CITRUS aurantium* (sweet orange) and *CITRUS aurantium* (orange blossom) pure essential oils.

A brightening cleanser is another example. Its ingredients can include organic juices of *PYRUS malus* (apple) juice (malic acid), *CITRUS medica* limonum (lemon) juice (citric acid), & *ALOE barbadensis* leaf juice, organic *SACCHARUM officinarum* (glycolic acid), organic botanical extract of melissa offficinalis (lemon balm) leaf, organic honey, tocopheryl acetate (vitamin E), glycerin, sodium carboxymethyl lauryl glucoside, cocamidopropyl betaine, sodium hydroxide, sclerotium gum, potassium sorbate, xanthan gum, benzyl alcohol, phenoxyethanol, disodium edta, azulene, linalool, geraniol, benzyl benzoate, and benzyl salicylate.

Further, the brightening cleanser described above can include Juice Beauty essential oils, such as *LITSEA cubeba* (may chang) & cananga odorata (ylang ylang) pure essential oils.

A vitamin antioxidant serum is another example. Its ingredients can include organic juices of *VITIS vinifera* (white grape) juice, *CITRUS aurantium* dulcis (orange) juice & *ALOE barbadensis* leaf juice, glycerin, organic essential fatty acids of *LINUM usitatissimum* (linseed) seed & *BORAGO officinali* (borage) seed, thioctic acid (alpha-lipoic acid), ubiquinone (coenzyme Q10), magnesium ascorbyl phosphate (vitamin C), dipeptide-2, palmitoyl tetrapeptide-3, tocopheryl acetate & tocopherol (vitamin E), sclerotium gum, phenoxyethanol, sodium hydroxide, benzyl alcohol, disodium edta, hyaluronic acid, and potassium sorbate.

Further, the vitamin antioxidant serum described above can include Juice Beauty essential oils, such as *AMYRIS balsamifera* & *LITSEA cubeba* (may chang) pure essential oils.

A brightening serum is another example. Its ingredients can include organic juices of *PYRUS malus* (apple) juice (malic acid), *CITRUS medica* limonum (lemon) juice (citric acid), organic *SACCHARUM officinarum* (glycolic acid), organic *ALOE barbadensis* leaf juice, glycerin, organic *CAMELLIA sinensis* (green tea) leaf extract, organic essential fatty acids of *LINUM usitatissimum* (linseed) seed & *BORAGO officinali* (borage) seed, ubiquinone (coenzyme Q10), thioctic acid (alpha-lipoic acid), dipeptide-2, palmitoyl tetrapeptide-3, magnesium ascorbyl phosphate (vitamin C), tocopheryl acetate & tocopherol (vitamin E), sclerotium gum, phenoxyethanol, sodium hydroxide, benzyl alcohol, disodium edta, phospholipids, hyaluronic acid, potassium sorbate, azulene, linalool, geraniol, benzyl benzoate, and benzyl salicylate.

Further, the brightening serum described above can include juice beauty essential oils, such as *LITSEA cubeba* (may chang) and cananga odorata (ylang ylang) pure essential oils.

A green apple body peel is another example. Its ingredients can include: organic juices of *PYRUS malus* (apple) juice (malic), *CITRUS medica* limonum (lemon) juice (citric) & *VITIS vinifera* (white grape) juice (tartaric), organic *SACCHARUM officinarum* (glycolic acid), organic milk peptides (lactic acid), organic *ALOE barbadensis* leaf juice, glycerin, hydroxypropyl starch phosphate, sodium hydroxide, organic algae extract, sclerotium gum, tocopheryl acetate & tocopherol (vitamin E), ascorbyl palmitate (vitamin C), retinyl palmitate (vitamin A), phospholipids, magnesium aspartate, zinc gluconate, copper gluconate, phenoxyethanol, benzyl alcohol, potassium sorbate, tetrasodium EDTA, xanthan gum, azulene.

A revitalizing eye treatment is another example. Its ingredients can include organic juices of *VITIS vinifera* (white grape) juice, *DAUCUS carota* sativa (carrot) juice & *ALOE barbadensis* leaf juice, organic *CUCUMIS sativus* (cucumber) extract, organic *HELIANTHUS annuus* (sunflower) oil, organic *CAMELLIA sinensis* (green tea) leaf extract, organic essential fatty acids of *LINUM usitatissimum* (linseed) seed & *BORAGO officinali* (borage) seed, glycerin, panthenol (vitamin B5), magnesium ascorbyl phosphate (vitamin C), tocopherol (vitamin E), cetearyl glucoside, phenoxyethanol, sodium hyaluronate, cetearyl alcohol, benzyl alcohol, potassium sorbate, xanthan gum, disodium edta, sodium hydroxide, limonene, linalool.

Further, the revitalizing eye treatment described above can include Juice Beauty essential oils, such as *CITRUS aurantium* (orange blossom) pure essential oil.

A SPF 20 Antioxidant Body Moisturizer is another example. Its active ingredients can include: titanium dioxide 2.5%. Its other ingredients can include: juices of *PYRUS malus* (apple) juice,* *CITRUS medica* limonum (lemon),* *VITIS vinifera* (white grape)* & *ALOE barbadensis* leaf,* saccarum officinarum,* *CAMELLIA sinensis* (green tea) leaf extract,* plant oils of *HELIANTHUS annuus* (sunflower), *BUTYROSPERMUM parkii* (shea butter)* & *SIMMONDSIA chinensis* (jojoba) seed,* essential fatty acids of *LINUM usitatissimum* (linseed) seed* & *BORAGO officinali* (borage) seed,* honey,* *CERA alba* (beeswax),* algae extract,* caprylic/capric triglyceride, glyceryl stearate, cetyl alcohol, stearyl alcohol, ubiquinone (coenzyme Q10), thioctic acid (alpha lipoic acid), palmitoyl tetrapeptide-3, magnesium ascorbyl phosphate (vitamin C), panthenol (vitamin B5), tocopheryl acetate (vitamin E), retinyl palmitate (vitamin A), allantoin, dimethylaminoethanol (DMAE), hyaluronic acid, sodium PCA, benzyl alcohol, phenoxyethanol, ethylhexylglycerin, limonene, and linalool. A (*) denotes certified organic by a USDA approved agency.

Further, the SPF 20 Antioxidant Body Moisturizer described above can include Juice Beauty essential oils, such as *CITRUS reticulata* (mandarin), *LITSEA cubeba* (may chang) and *CINNAMOMUM camphora* (ho wood) pure essential oils.

A daily nourishing moisturer is another example. Its ingredients can include: organic juices of *VITIS vinifera* (white grape) juice, *DAUCUS carota* sativa (carrot) juice & *ALOE barbadensis* leaf juice, organic botanical extracts of *CALENDULA officinalis* flower & *MATRICARIA chamomilla* flower, organic *BUTYROSPERMUM parkii* (shea butter), organic essential fatty acids of *LINUM usitatissimum* (linseed) seed & *BORAGO officinali* (borage) seed, glycerin, organic honey, squalane, tocopheryl acetate (vitamin E), magnesium ascorbyl phosphate (vitamin C), hyaluronic acid, hydroxypropyl starch phosphate, glyceryl stearate, potassium sorbate, beta carotene, stearic acid, cetearyl glucoside, xanthan gum, disodium edta, sodium hydroxide, benzyl alcohol, phenoxyethanol, linalool, geraniol, benzyl benzoate, and benzyl salicylate.

Further, the daily nourishing moisturer described above can include Juice Beauty essential oils, such as *LITSEA cubeba* (may chang), cananga odorata (ylang ylang) & *BOSWELLIA carterii* (frankincense) pure essential oils.

A brightening moisturizer is another example. Its ingredients can include: organic juices of *PYRUS malus* (apple) juice (malic acid), *CITRUS medica* limonum (lemon) juice (citric acid) & *VITIS vinifera* (white grape) juice (tartaric acid), organic *SACCHARUM officinarum* (glycolic acid), organic *ALOE barbadensis* leaf juice, glycerin, organic *CAMELLIA sinensis* (green tea) leaf extract, organic plant oils of *BUTYROSPERMUM parkii* (shea butter) & *SIMMONDSIA chinensis* (jojoba) seed, organic honey, organic essential fatty acids of *LINUM usitatissimum* (linseed) seed & *BORAGO officinali* (borage) seed, ubiquinone (coenzyme Q10), thioctic acid (alpha-lipoic acid), dipeptide-2, palmitoyl tetrapeptide-3, magnesium ascorbyl phosphate (vitamin C), tocopheryl acetate & tocopherol (vitamin E), phenoxyethanol, sodium hydroxide, benzyl alcohol, disodium edta, phospholipids, hyaluronic acid, potassium sorbate, azulene, linalool, geraniol, benzyl benzoate, and benzyl salicylate.

Further, the brightening moisturer described above can include Juice Beauty essential oils, such as *LITSEA cubeba* (may chang) and cananga odorata (ylang ylang) pure essential oils.

A lip amplifier is another example. Its ingredients can include: organic juices of *CITRUS aurantium* dulcis (orange) juice & *ALOE barbadensis* leaf juice, organic *SIMMONDSIA chinensis* (jojba) seed oil, glycerin, organic honey, organic essential fatty acids of *LINUM usitatissimum* (linseed) seed & *BORAGO officinali* (borage) seed, tocopheryl acetate & tocopherol (vitamin E), ascorbyl palmitate (vitamin C), caprylic/capric triglyceride, ethylhexyl (octyl) palmitate, tribehenin, sorbitan isostearate, palmitoyl oligopeptide, glyceryl stearate, sorbitan stearate, phospholipids, organic *SACCHARUM officinarum* (glycolic acid), palmitic acid, stearic acid, cetearyl glucoside, xanthan gum, potassium sorbate, benzyl alcohol, phenoxyethanol, limonene, and linalool.

Further, the lip amplifier described above can include Juice Beauty essential oils, such as *CITRUS aurantium* (sweet orange) pure essential oil.

A tinted lip amplifier is another example. Its ingredients can include: organic *ALOE barbadensis* leaf juice, organic *BUTYROSPERMUM parkii* (shea butter), organic *HELIANTHUS annuus* (sunflower) oil, organic *CERA alba* (beeswax), mica & iron oxides (mineral tints), *COPERNICIA cerifera* (carnauba) wax, organic *PSIDIUM guajava* (guava), *RUBUS idaeus* (raspberry) & *VACCINIUM macrocarpon* (cranberry) fruit extracts, organic *PRUNUS persica* (peach) kernel oil, organic *SIMMONDSIA chinensis* (jojoba) seed oil, octyldodecanol, organic SACCHARUM officinarum (glycolic acid), cetearyl glucoside, cetearyl alcohol, ascorbyl palmitate (vitamin C), tocopherol (vitamin E), organic honey, organic *PERSEA gratissima* (avocado) oil, ethylhexyl (octyl) palmitate, tribehenin, sorbitan isostearate, palmitoyl oligopeptide, citric acid, limonene, linalool.

Further, the tinted lip amplifier described above can include Juice Beauty essential oils, such as *CITRUS aurantium* (sweet orange) pure essential oil.

Green Apple eye cream is another example of an organic, juice-based skin care product. In one embodiment, such an eye cream can comprise an organic juice base, e.g., of organic juices of *PYRUSi malus* (apple) juice, *DAUCUS carota* sativa (carrot) juice, and *ALOE barbadensis* leaf juice, organic *CUCUMIS sativus* (cucumber) extract, organic plant oils of *HELIANTHUS annuus* (sunflower), and *PERSEA gratissima* (avocado), *CAMELLIA sinensis* (organic green tea) leaf extract, organic essential fatty acids of *OENOTHERA biennis* (evening primrose), *LINUM usitatissimum* (linseed) seed, and *BORAGO officinali* (borage) seed, glycerin, *LIMNANTHES alba* (meadow foam) seed oil, phytonadione (vitamin K1), retinyl palmitate (vitamin A), magnesium ascorbyl phosphate (vitamin C), tocopherol (vitamin E), cetearyl glucoside, ubiquinone (coenzyme Q10), thioctic acid (alpha-lipoic acid), dimethylaminoethanol (DMAE), dipeptide-2, palmitoyl tetrapeptide-3, phenoxyethanol, hesperidin methyl chalcone (vitamin P), sodium hyaluronate, cetearyl alcohol, benzyl alcohol, potassium sorbate, steareth-20, xanthan gum, tetrasodium edta, sodium hydroxide, azulene, and *CITRUS aurantium* (orange blossom) pure essential oil.

The eye cream ingredients described above can be used to compose a powerful complex of age-defying DMAE, vitamin antioxidants, alpha lipoic acid and co-enzyme Q10, combined with essential nutrients and peptides to hydrate, smooth lines, and help firm the area around the eyes.

Further, azulene and apple juice can be added to the ingredients to form a green apple nutrient eye cream. The green apple eye cream can have a green apple smell and color.

Cleansing milk is another example of an organic, juice-based skin care product. In one embodiment, such cleansing milk can comprise an organic juice base of organic juices of *VITIS vinifera* (white grape) juice, *RUBUS idaeus* (red raspberry) juice, and *ALOE barbadensis* leaf juice, organic botanical extracts of *CALENDULA officinalis* flower, *MATRICARIA chamomilla* flower, and *TILIA europea* (linden) leaf, glycerin, organic plant oils of carthamus tinctorius (safflower) seed, *PRUNUS amygdalus* dulcis (sweet almond), *HELIANTHUS annuus* (sunflower), and *SESAMUM indicum* (sesame), *VITIS vinifera* (grape) seed oil, caprylic/capric triglyceride, cetearyl alcohol, cetearyl glucoside, tocopheryl acetate, and tocopherol (vitamin E), sorbitan stearate, retinyl palmitate (vitamin A), phospholipids, ascorbyl palmitate (vitamin C), tetrasodium edta, panthenol (vitamin B5), allantoin, phenoxyethanol, xanthan gum, benzyl alcohol, potassium sorbate, and citric acid.

Further, the cleansing milk product described above can include Juice Beauty essential oils, such as *CITRUS aurantium* (sweet orange and orange blossom), *ANTHEMIS nobilis* (chamomile), and *BOSWELLIA carterii* (frankincense) pure essential oils.

A tinted lip moisturizer can be another example of an organic, juice-based skin care product. In one embodiment, an organic, juice based tinted lip moisturizer can comprise plant oils of *COCOS nucifera* (coconut)* and *HELIANTHUS annuus* (sunflower)* infused with *PSIDIUM guajava* (guava), and *PRUNUS persica* (peach) fruit essences, *BUTYROSPERMUM parkii* (shea butter) fruit,* *CERA alba* (beeswax),* *EUPHORBIA cerifera* (candelilla) wax,* *COPERNICIA cerifera* (carnauba) wax, *SIMMONDSIA chinensis* (jojoba) seed oil,* titanium dioxide, panthenol (vitamin B5), lecithin, honey,* ascorbyl palmitate (vitamin C), *ALOE barbadensis* leaf juice,* algae extract,* and tocopherol (vitamin E). A (*) denotes certified organic by a USDA approved agency.

The tinted lip moisturizer can also comprise natural tints that can include, e.g., mica and iron oxides, but no fdc colors or carmine.

Further, this embodiment of a tinted lip moisturizer can comprise as active ingredients: octinoxate and oxybenzone.

Lip plumper is another example of an organic, juice-based skin care product. In one embodiment, such a lip plumper product can comprise an organic juice base of organic juices of *CITRUS aurantium* dulcis (orange) juice, and *ALOE barbadensis* leaf juice, organic *SIMMONDSIA chinensis* (jojoba) seed oil, glycerin, organic honey, organic essential fatty acids of *OENOTHERA biennis* (evening primrose), *LINUM usitatissimum* (linseed) seed, and *BORAGO officinali* (borage) seed, tocopheryl acetate, and tocopherol (vitamin E), retinyl palmitate (vitamin A), ascorbyl palmitate (vitamin C), caprylic/capric triglyceride, ethylhexyl (octyl) palmitate, tribehenin, sorbitan isostearate, palmitoyl oligopeptide, glyceryl stearate, sorbitan stearate, phospholipids, glycolic acid, palmitic acid, stearic acid, cetearyl glucoside, xanthan gum, potassium sorbate, benzyl alcohol, and phenoxyethanol.

Further, the lip plumper product described above can include Juice Beauty essential oils, such as citrus tangerina and *CINNAMOMUM cassia* leaf (cinnamon) pure essential oils. Such a lip plumper can also comprise other Juice Beauty pure essential oils.

Another example organic, juice based product is a blemish clearing serum composed so as to prevent and heal blemishes and even out skin tone and texture. Such a blemish clearing product can comprise an organic juice base of juices of *PYRUS malus* (apple) juice,* *CITRUS medica* limonum (lemon) juice,* and *ALOE barbadensis* leaf juice,* raw cane sugar (glycolic),* *SALIX alba* (willow bark) extract, glycerin, botanical extracts of *TARAXACUM officinale* (dandelion) leaf,* *MELISSA officinalis* (lemon balm) leaf,* *SALVIA officinalis* (sage) leaf,* and *CAMELLIA sinensis* (green tea) leaf,* algae extract,* ubiquinone (coenzyme Q10), magnesium ascorbyl phosphate (vitamin C), tocopheryl acetate (vitamin E), retinyl palmitate (vitamin A), panthenol (vitamin B5), allantoin, phospholipids, sodium hydroxide, sclerotium gum, phenoxyethanol, benzyl alcohol, potassium sorbate, tetrasodium edta, xanthan gum, lavandula angustifolia, and *COMMIPHORA myrrha* pure essential oils. A (*) denotes certified organic by a USDA approved agency.

Another example of an organic, juice-based product is a green apple nutrient mask that can be composed to deliver vitamin antioxidants to nourish, hydrate and revitalize protective surfaces on exfoliated skin. Such a green apple nutrient mask can comprise an organic juice base of organic juices of *PYRUSi malus* (apple) juice, CITRUS medica limonum (lemon) juice, VITIS vinifera (white grape) juice, and *ALOE barbadensis* leaf juice, organic essential fatty acids of OENOTHERA biennis (evening primrose), LINUM usitatissimum (linseed) seed, and BORAGO officinali (borage) seed, organic honey, VITIS vinifera (grape) seed oil, glycerin, sodium hydroxide, sodium hyaluronate, *PYRUSi malus* (apple) pectin, organic botanical extracts of ROSE canina (rosehip) fruit, and CAMELLIA sinensis (green tea) leaf, organic algae extract, caprylic/capric triglyceride, glyceryl stearate, stearic acid, sodium pca, ubiquinone (coenzyme Q10), thioctic acid (alpha-lipoic acid), dipeptide-2, palmitoyl tetrapeptide-3, magnesium ascorbyl phosphate (vitamin C), tocopheryl acetate (vitamin E), retinyl palmitate (vitamin A), hydroxypropyl starch phosphate, sclerotium gum, phenoxyethanol, xanthan gum, benzyl alcohol, potassium sorbate, tetrasodium edta.

Further, the ingredient for the green apple nutrient mask described above can include Juice Beauty pure essential oils, such as *CITRUS reticulata* (mandarin), *LITSEA cubeba* (may chang), and *CINNAMOMUM camphora* (ho wood) pure essential oils.

Further, as noted azulene can be added to the ingredients in order to give the serum a green apple color.

Another example of an organic, juice-based product is an exfoliating cleanser that can be composed to gently cleanse and exfoliate, removing dull, lack-luster skin for a brighter, refined complexion. Such an exfoliating cleanser can comprise an organic juice base of organic juices of *VITIS vinifera* (white grape) juice, *ANANAS sativus* (pineapple) juice, and *ALOE barbadensis* leaf juice, organic plant oils of *SESAMUM indicum* (sesame) seed, *PRUNUS amygdalus dulcis* (sweet almond), *BUTYROSPERMUM parkii* (shea butter), *PERSEA gratissima* (avocado), and *SIMMONDSIA chinensis* (jojoba wax) seed, organic botanical extracts of *CALENDULA officinalis* flower, *MATRICARIA chamomilla* flower, and *TILIA europea* (linden) leaf, caprylic/capric triglyceride, glycerin, organic honey, organic algae extract, glyceryl stearate, tocopheryl acetate (vitamin E), retinyl palmitate (vitamin A), ascorbyl palmitate (vitamin C), potassium sorbate, phospholipids, hydroxypropyl starch phosphate, benzyl alcohol, sodium pca, palmitic acid, stearic acid, cetearyl glucoside, xanthan gum, disodium edta, sodium hydroxide, and phenoxyethanol. Such an exfoliating cleanser can also comprise Juice Beauty pure essential oils.

Another example of an organic, juice-based product is a smoothing eye concentrate that can be composed to help reduce puffiness and help brighten the area under the eye. Such a smoothing eye concentrate can comprise a blend of organic grape and carrot juice with essential fatty acids and vitamins B5, C, E, K, and P to hydrate, help smooth fine lines, and help brighten the eye area.

Specifically, such a smoothing eye concentrate can comprise an organic juice base of organic juices of *VITIS vinifera* (white grape) juice, *DAUCUS carota* sativa (carrot) juice, and *ALOE barbadensis* leaf juice, organic *CUCUMIS sativus* (cucumber) extract, organic plant oils of *HELIANTHUS annuus* (sunflower), and *PERSEA gratissima* (avocado), *CAMELLIA sinensis* (organic green tea) leaf extract, organic algae extract, organic essential fatty acids of *OENOTHERA biennis* (evening primrose), *LINUM usitatissimum* (linseed) seed, and *BORAGO officinali* (borage) seed, glycerin, *LIMNANTHES alba* (meadow foam) seed oil, phytonadione (vitamin K1), panthenol (vitamin B5), retinyl palmitate (vitamin A), magnesium ascorbyl phosphate (vitamin C), tocopherol (vitamin E), cetearyl glucoside, phenoxyethanol, hesperidin methyl chalcone (vitamin P), sodium hyaluronate, cetearyl alcohol, benzyl alcohol, potassium sorbate, steareth-20, xanthan gum, tetrasodium edta, sodium hydroxide. Such a smoothing eye concentrate can also comprise Juice Beauty pure essential oils.

Another example of an organic, juice-based product is a cleansing gel that can be composed to purify and balance oily, combination, and blemished skin without over drying. Such a cleansing gel can comprise an organic juice base of organic juices of *CITRUS medica* limonum (lemon) juice, prunus avium (sweet cherry) juice, *VITIS vinifera* (red grape) juice, and *ALOE barbadensis* leaf juice, organic botanical extracts of *TARAXACUM officinale* (dandelion) leaf, *MELISSA officinalis* (lemon balm) leaf, and *SALVIA officinalis* (sage) leaf, sodium carboxymethyl lauryl glucoside, cocamidopropyl betaine, glycerin, sodium hydroxide, tocopheryl acetate (vitamin E), retinyl palmitate (vitamin A), organic algae extract, potassium sorbate, xanthan gum, sclerotium gum, benzyl alcohol, phenoxyethanol, and disodium edta. Such a cleansing gel can also comprise Juice Beauty pure essential oils.

Another example of an organic, juice-based product is green apple cleansing gel. Such a cleansing gel can have the following ingredients: organic juices of *PYRUS malus* (apple) juice, *CITRUS medica* limonum (lemon) juice, *VITIS vinifera* (white grape) juice, and *ALOE barbadensis* leaf juice, organic raw cane sugar (glycolic), organic botanical extracts of *TARAXCUM officinale* (dandelion) leaf, *MELISSA officinalis* (lemon balm) leaf, and *SALVIA officinalis* (sage) leaf, organic honey, organic algae extract, tocopheryl acetate (vitamin E), retinyl palmitate (vitamin A), glycerin, sodium carboxymethyl lauryl glucoside, cocamidopropyl betaine, sodium hydroxide, sclerotium gum, potassium sorbate, xanthan gum, benzyl alcohol, phenoxyethanol, disodium edta, and azulene.

Further, the green apple cleansing gel product described above can include Juice Beauty essential oils, such as *CITRUS reticulata* (mandarin), *LITSEA cubeba* (may chang), and *CINNAMOMUM camphora* (ho wood) pure essential oils.

Another example of an organic, juice-based product is a Green Apple peel that can be composed to reveal glowing, healthy skin. The peel product can include the following ingredients: an organic juice base of organic hydroxy-acid juices of *PYRUSi malus* (apple) juice (malic), *CITRUS medica* limonum (lemon) juice (citric), and *VITIS vinifera* (white grape) juice (tartaric), organic raw cane sugar (glycolic), *SALIX alba* (willow bark) extract (salicylic), organic milk peptides (lactic), and organic *ALOE barbadensis* leaf juice.

Such an organic, juice based green apple peel product can also include glycerin, hydroxypropyl starch phosphate, sodium hydroxide, organic algae extract, sclerotium gum, tocopheryl acetate & tocopherol (vitamin E), ascorbyl palmitate (vitamin C), retinyl palmitate (vitamin A), phospholipids, magnesium aspartate, zinc gluconate, copper gluconate, phenoxyethanol, benzyl alcohol, potassium sorbate, tetrasodium edta, xanthan gum, azulene.

As noted azulene can be added to the ingredients in order to give the serum a green apple color.

Zinc gluconate is a combination of zinc with a form of glucose (a sugar) that is commonly used in cold lozenges for its antiviral effects. A study reported in Dermatology (2001, volume 203, issue 2, page 40), which is incorporated herein in its entirety as if set forth in full, evaluated "the place of zinc gluconate in relation to antibiotics in the treatment of acne vulgarism Zinc was compared to minocycline [an antibiotic] in a multicenter randomized double-blind trial. 332 patients received either 30 milligrams elemental zinc or 100 milligrams minocycline over 3 months. The primary endpoint was defined as the percentage of the clinical success rate on day 90 . . . " The study concluded that "Minocycline and zinc gluconate are both effective in the treatment of inflammatory acne, but minocycline has a superior effect evaluated to be 17% in our study." Whether or not this relates to topical applications is unknown. Note: high doses of zinc can be toxic. Avoid taking more than 100 mg of zinc per day from a supplement (Source: www.drweil.com). It is also recommended that a daily multivitamin with minerals be taken because increases levels of zinc mean that the body requires more copper and manganese.

Copper gluconate is included because copper is an important trace element for human nutrition. The body needs copper to absorb and utilize iron, and copper is also a component of the powerful antioxidant enzyme superoxide dismutase. Copper supplements have been shown to increase superoxide dismutase levels in humans as noted in: Healthnotes Review of Complementary and Integrative Medicine, www.healthnotes.com, which is incorporated herein in its entirety as if set forth in full. The synthesis of collagen and elastin is in part related to the presence of copper in the body, and copper is also important for many other processes. For example, there is research showing that copper is effective for wound healing as noted in: Journal of Clinical Investigation, November 1993, pages 2368-2376: and Federation of European Biochemical Sciences Letter, October 1988, pages 343-346, which are both incorporated herein in their entirety as if set forth in full. However, wound healing is the result of many biophysical processes that have nothing to do with wrinkling.

Phospholipids is a type of lipid (fat) composed of glycerol, fatty acids, and phosphate. Phopholipids are essential to the function of cell membranes by providing a stable surrounding structure. Lecithin and cholesterol are phosopholipids.

Magnesium aspartate is an amino acid chelate of Magnesium and Aspartic Acid. This complex forms a tight bond and is released in the inner layer of the outer cell membrane.

Amino acids are fundamental constituents of all proteins found in the body, such as: alanine, arginine, asparagines, asparatic acid, cysteine, cystine, glutamic acid, glutamine, glycine, histidine, isoleucine, leucine, lysine, methionine, phenylalanine, proline, serine, threonine, tryptophan, tyrosine, and valine. Some of these amino acids can be synthesized by the body; others, the essential amino acids, must be obtained from protein in the diet. In skin-care products, these types of ingredients work primarily as water-binding agents, and some have antioxidant properties and wound-healing abilities as well. However, these substances cannot affect, change, or rebuild wrinkles. Whether the protein in a skin-care product is derived from an animal or a plant, the skin can't tell the difference.

EDTA is the abbreviation for ethylenediaminetetraacetic acid, which can also be included. It is a stabilizer used in cosmetics to prevent ingredients in a given composition from binding with trace elements (particularly minerals) that can exist in water and other ingredients to cause unwanted product changes such as texture, odor, and consistency problems. The technical term for this function is a chelating agent.

Another example of an organic, juice-based product is an oil-free moisturizer that can be composed to protect and nourish normal and oily skin. Such an oil-free moisturizer can include an organic juice base of organic juices of *PYRUS malus* (apple) juice, *VITIS vinifera* (white grape) juice, *PUNICA granatum* (pomegranate) juice, and *ALOE barbadensis* leaf juice, organic *CUCUMIS sativus* (cucumber) extract, organic botanical extracts of *TARAXACUM officinale* (dandelion) leaf, *MELISSA officinalis* (lemon balm) leaf, and *SALVIA officinalis* (sage) leaf, glycerin, caprylic/capric triglyceride, alkyl benzoate, retinyl palmitate (vitamin A), panthenol (vitamin B5), tocopheryl acetate (vitamin E), organic algae extract, organic *CERA alba* (beeswax), ascorbyl palmitate (vitamin C), ethylhexyl (octyl) palmitate, cetearyl alcohol, cetearyl glucoside, sodium pca, sodium hyaluronate, xanthan gum, disodium edta, sodium hydroxide, phenoxyethanol. Such an oil-free moisturizer can also comprise Juice Beauty pure essential oils.

Another example of an organic, juice-based product is soothing serum that can be composed to help alleviate redness, calm circulatory stress, and restore healthy skin tone. Such a soothing serum can include an organic juice base of organic juices of *VITIS vinifera* (white grape) juice, *RUBUS idaeus* (red raspberry) juice, and *ALOE barbadensis* leaf juice, glycerin, organic *CUCUMIS sativus* (cucumber) extract, organic botanical extracts of *GLYCYRRHIZA glabra* (licorice) root, *ARCTPSTAPHYLOS uvaursi* (bear berry) leaf, *RUBUS idaeus* (red raspberry) leaf, *CALENDULA officinalis* flower, and *MATRICARIA chamomilla* flower, organic algae extract, *VITIS vinifera* (grape) seed oil, organic essential fatty acids of *OENOTHERA biennis* (evening primrose), *LINUM usitatissimum* (linseed) seed, and *BORAGO officinali* (borage) seed, organic *SESAMUM indicum* (sesame) seed oil, tocopherol, and tocopheryl acetate (vitamin E), panthenol (vitamin B5), magnesium ascorbyl phosphate (vitamin C), phospholipids, retinyl palmitate (vitamin A), hesperidin methyl chalcone, potassium sorbate, hyaluronic acid, sclerotium gum, phenoxyethanol, benzyl alcohol, disodium edta, and sodium hydroxide. Such soothing serum can also comprise Juice Beauty pure essential oils.

Another example of an organic, juice based skin care product is a sheer moisturizer that can include an active ingredient of titanium dioxide, as well as organic juice base of: juices of *PYRUSi malus* (apple) juice,* *VITIS vinifera* (white grape) juice,* *PUNICA granatum* (pomegranate) juice,* and *ALOE barbadensis* leaf juice,* *CUCUMIS sativus* (cucumber) fruit extract,* *CAMELLIA sinensis* (green tea) leaf extract,* *CERA alba* (beeswax),* octyl palmitate, caprylic/capric triglyceride, glycerin, cetearyl alcohol, cetearyl glucoside, plant oils of *HELIANTHUS annuus* (sunflower),* *PERSEA gratissima* (avocado),* and *SIMMONDSIA chinensis* (jojoba) seed,* tocopheryl acetate (vitamin E), sodium pca, sodium hyaluronate, retinyl palmitate (vitamin A), phospholipids, panthenol (vitamin B5), ascorbyl palmitate (vitamin C), xanthan gum, tetrasodium edta, phenoxyethanol, *CITRUS aurantium* (petitgrain), *CINNAMOMUM camphora* (ho wood), and *CITRUS reticulata* (mandarin) pure essential oils. A (*) denotes certified organic by a USDA approved agency.

Another example of an organic, juice based skin care product is a tinted moisturizer that can include an active ingredient of Titanium Dioxide, as well as organic juice base of: juices of *PYRUSi malus* (apple) juice,* *VITIS vinifera* (white grape) juice,* *PUNICA granatum* (pomegranate) juice,* and *ALOE barbadensis* leaf juice,* *CUCUMIS sativus* (cucumber) fruit extract,* *CAMELLIA sinensis* (green tea) leaf extract,* *CERA alba* (beeswax),* octyl palmitate, caprylic/capric triglyceride, glycerin, cetearyl alcohol, cetearyl glucoside, plant oils of *HELIANTHUS annuus* (sunflower),* *PERSEA gratissima* (avocado),* and *SIMMONDSIA chinensis* (jojoba) seed,* tocopheryl acetate (vitamin E), sodium pca, sodium hyaluronate, retinyl palmitate (vitamin A), phospholipids, panthenol (vitamin B5), ascorbyl palmitate (vitamin C), xanthan gum, tetrasodium edta, phenoxyethanol, mica & iron oxides (mineral tints), *CITRUS aurantium* (petitgrain), *CINNAMOMUM camphora* (ho wood), and *CITRUS reticulata* (mandarin) pure essential oils. A (*) denotes certified organic by a USDA approved agency Another example of an organic, juice-based product is a hydrating mist that can be composed to hydrate and balance the skin's natural moisture. Such a hydrating mist can include an organic juice base of organic juices of *VITIS vinifera* (white and red grape) juice, and *ALOE barbadensis* leaf juice, glycerin, *VITIS vinifera* (grape) seed oil, tocopheryl acetate & tocopherol (vitamin E), organic *ROSE canina* (rosehip) fruit extract, *A VENA sativa* (oat) extract, (retinyl palmitate (vitamin A), *CITRUS grandis* (grapefruit) seed extract, ascorbyl palmitate (vitamin C), phospholipids, lecithin, phenoxyethanol, benzyl alcohol, potassium sorbate, sodium hydroxide, tetrasodium edta, citric acid, rosa damascena, and cananga odorata (ylang ylang) pure essential oils.

Again, these are just some of the example organic, juice based skin care products that can be composed according to the processes described herein.

Figure 2:
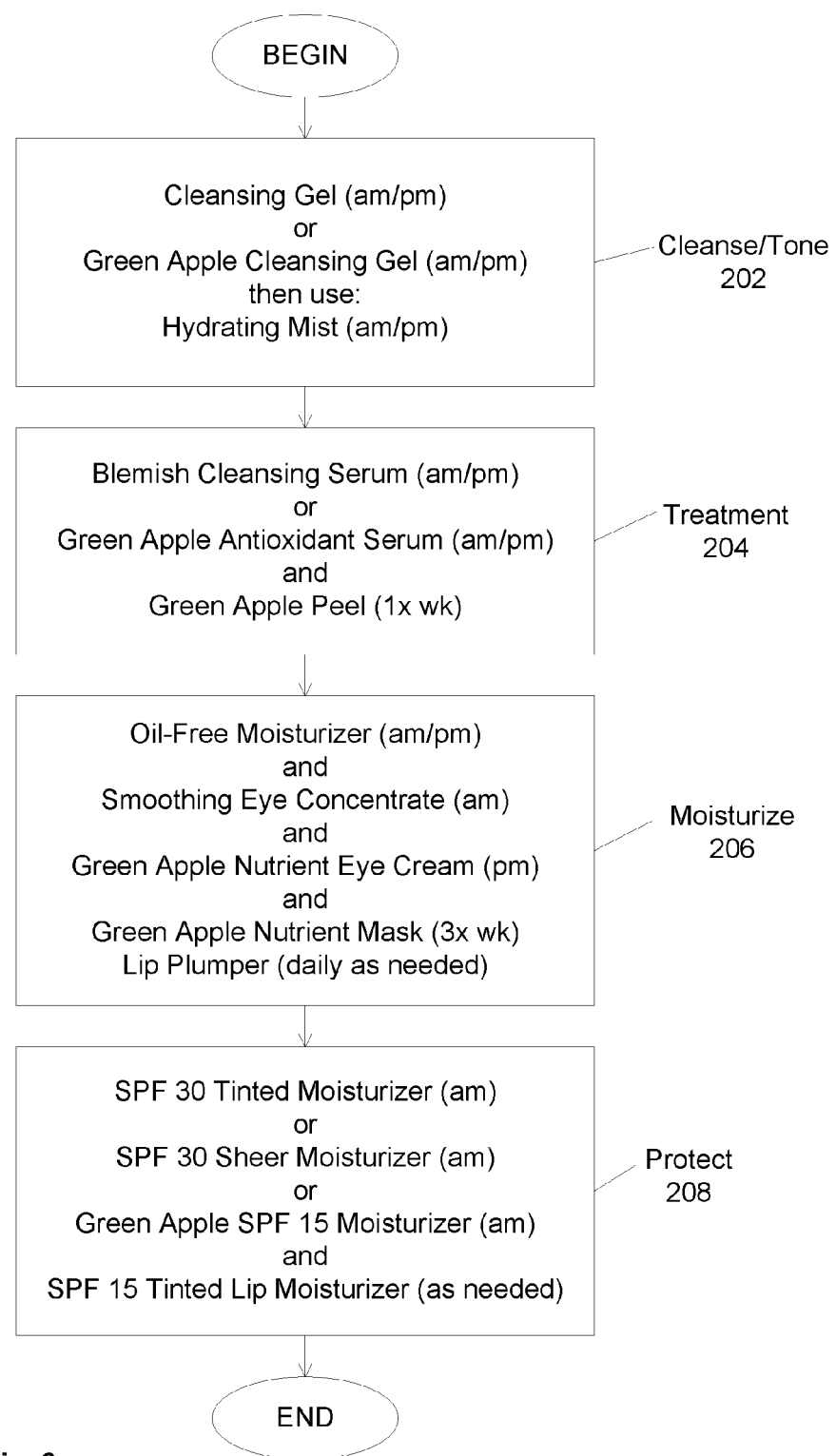
FIG. 2 is a flowchart illustrating another example skin care solution that makes use of organic skin care products in accordance with another embodiment.
Figure 3:
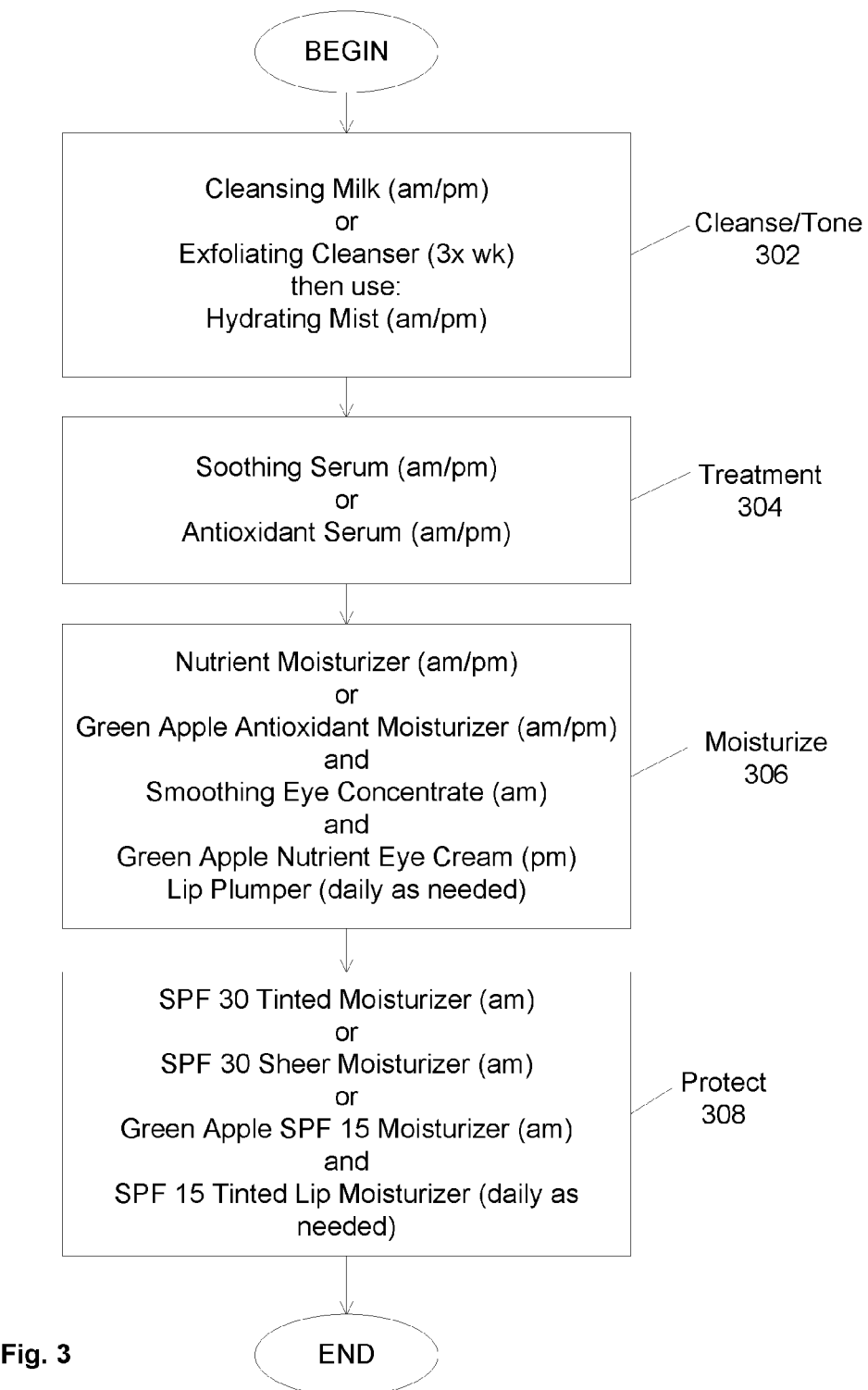
FIG. 3 is a flowchart illustrating another example skin care solution that makes use of organic skin care products in accordance with still another embodiment.

Further, the organic, juice based skin care products can be used in different combinations to achieve different skin treatment solutions as required. FIGS. 1-3 illustrated a few example solutions; however, it will be clear that the number and type of solutions is vast. In each of the solutions depicted in FIGS. 1-3, a cleanse and tone step is followed by a treatment step, a moisturizing step, and a protection step. It will be understood that the cleanse/tone, treatment, and moisturize steps should be performed routinely, e.g., every morning and night, while the protection step can be applied as needed. Further, it will be apparent that steps can be included and/or excluded as needed to achieve a certain treatment solution.

In FIG. 1, the cleanse and tone step 102 comprises applying organic, juice based cleansing milk, exfoliating cleanser, or green apple cleansing gel. The cleansing product selected can be applied in the morning and in the evening. After cleansing a hydrating mist can be used to tone the skin. Example descriptions of these products can be found above. The treatment step 104 comprises applying one or more organic, juice based antioxidant serums. The antioxidant serums can be applied in the morning and in the evening and can be followed by a green apple peel once per week. Again, example descriptions of these products can be found above.

The moisturizing step 106 can comprise applying an organic, juice based nutrient moisturizer or a green apple antioxidant moisturizer in the morning and in the evening, followed by a smoothing eye concentrate in the morning, and a green apple nutrient eye cream in the evening, and lip plumper as needed. Again, example descriptions of these products can be found above. The protective step 108 can comprise applying spf 30 tinted moisturizer, spf 30 sheer moisturizer or green apple spf 15 moisturizer in the morning and spf 15 tinted lip moisturizer as needed.

The solution of FIG. 1, can for example, be used to replenish dry to normal or aging skin.

In FIG. 2, the cleanser and tone step 202 comprises applying one or more organic, juice based cleansing gels, for example, green apple cleansing gel. The cleansing gel can be applied in the morning and the evening followed by a hydrating mist. Example descriptions of these products can be found above. The treatment step 204 comprises applying organic, juice based blemish clearing serum or green apple antioxidant serum in the morning and the evening, and a green apple peel once per week. Again, example descriptions of these products can be found above.

The moisturizing step 206 can comprise applying an organic, juice based oil-free moisturizer in the morning and the evening and a smoothing eye concentrate in the morning and a green apple nutrient eye cream in evening. A green apple nutrient mask can be applied three times per week, and lip plumper can be applied as needed. Again, example descriptions of these products can be found above. The protective step 208 can comprise applying spf 30 tinted, spf 30 sheer moisturizer, or green apple spf 15 tinted lip moisturizer in the morning and spf 15 tinted lip moisturizer as needed.

The solution of FIG. 2, can for example, be used to clarify blemish prone oily or combination skin problems.

In FIG. 3, the cleanse and tone step 302 comprises applying organic, juice based cleansing milk in the morning and the evening or an exfoliating cleanser three times per week followed by a hydrating mist in the morning and the evening. Example descriptions of these products can be found above. The treatment step 304 comprises applying organic, juice based soothing serum or an antioxidant serum in the morning and the evening. Again, example descriptions of these products can be found above.

The moisturizing step 306 can comprise applying an organic, juice based nutrient moisturizer or a green apple antioxidant moisturizer in the morning and the evening followed by a smoothing eye concentrate in the morning and a green apple nutrient eye cream in the evening, and lip plumper as needed. Again, example descriptions of these products can be found above. The protective step 308 can comprise applying spf 30 tinted moisturizer, spf 30 sheer moisturizer, or green apple spf 15 moisturizer in the morning, and spf 15 tinted lip moisturizer daily as needed.

The solution of FIG. 3, can for example, be used to soothe sensitive, aging, and/or redness prone skin.

While certain embodiments of the inventions have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed:

1. A juice-based skin peel composition comprising a blend of organic juices and other organic ingredients, wherein the blend of organic juices and other organic ingredients comprise at least 70% by weight of the composition; said composition comprising *Pyrus malus* (apple) juice, *Citrus medica limonum* (lemon) juice, *Vitis vinfera* (white grape) juice, *Saccharum officinarum*, milk peptides, *Aloe barbadensis* leaf juice, glycerin, hydroxypropyl starch phosphate, sodium hydroxide, algae extract, sclerotium gum, tocopherol acetate and tocopherol (vitamin E), ascorbyl palmitate (vitamin C), retinyl palmitate (vitamin A), phospholipids, magnesium aspartate, zinc gluconate, copper gluconate, phenoxyethanol, benzyl alcohol, potassium sorbate, tetrasodium EDTA and xanthan gum.

2. The skin peel composition of claim 1, further comprising *Salix alba* (willow bark) extract (salicylic).

3. The skin peel composition of claim 1, further comprising azulene.

4. A juice-based facial mask composition comprising a blend of organic juices and other organic ingredients, wherein the blend of organic juices and other organic ingredients comprise at least 70% by weight of the composition; said composition comprising *Pyrus malus* (apple) juice, *Citrus medica* limonum (lemon) juice, *Vitis vinfera* (white grape) juice, *Aloe barbadensis* leaf juice, essential fatty acids of *Oenothera biennis* (evening primrose), *Linumusitatissimum* (linseed) seed, *Borago officinali* (borage) seed, honey, *Vitis vinfera* (grape) seed oil, glycerin, sodium hydroxide, sodium hyaluronate, *Pyrus malus* (apple) pectin, botanical extracts of *Rose canina* (rosehip) fruit, *Camellia sinensis* (green tea) leaf, algae extract, caprylic/capric triglyceride, glycerol stearate, stearic acid, sodium PCA, ubiquinone (coenzyme Q10), thioctic acid (alpha-lipoic acid), dipeptide-2, palmitoyl tetrapeptide-3, magnesium ascorbyl phosphate (vitamin C), tocopherol acetate (vitamin E), retinyl palmitate (vitamin A), hydroxylpropyl starch phosphate, sclerotium gum, phenoxyethanol, xanthan gum, benzyl alcohol, potassium sorbate and tetrasodium EDTA.

5. The facial mask composition of claim 4, further comprising azulene.

6. The facial mask composition of claim 4, further comprising essential oils.

7. The facial mask composition of claim 6, wherein the essential oils include *Citrus reticulata* (mandarin) oil.

8. The facial mask composition of claim 6, wherein the essential oils include *Litsea cubea* (may chang).

9. The facial mask composition of claim 6, wherein the essential oils include *Cinnamomum campora* (ho wood) oil.

* * * * *